United States Patent [19]

Kronner

[11] 4,037,592
[45] July 26, 1977

[54] GUIDE PIN LOCATING TOOL AND METHOD

[76] Inventor: Richard F. Kronner, Rte. 2, Box 583, Roseburg, Oreg. 97470

[21] Appl. No.: 682,833

[22] Filed: May 4, 1976

[51] Int. Cl.² .................... A61B 17/18; A61F 5/04
[52] U.S. Cl. .................................................. 128/92 EB
[58] Field of Search .......... 128/92 EB, 92 E, 92 BA, 128/92 R, 92 F, 83

[56] References Cited

U.S. PATENT DOCUMENTS

| 2,301,500 | 11/1942 | Anderson | 128/92 EB |
| 2,697,433 | 12/1954 | Zehnder | 128/92 EB X |

FOREIGN PATENT DOCUMENTS

| 483,292 | 3/1917 | France | 128/92 EB |
| 240,542 | 4/1946 | Sweden | 128/92 EB |

OTHER PUBLICATIONS

"Boppe's Goniograh," Advertisement page 25 for the Medical Supply Assoc., Ltd. (London) in the Journal of Bone & Joint Surgery (British Edition), Nov. 1948.

*Primary Examiner*—Ronald L. Frinks
*Attorney, Agent, or Firm*—James D. Givnan, Jr.

[57] ABSTRACT

A tool and method for use by a surgeon in the insertion of a hip nail guide pin within upper end of a femur. The tool includes a base for temporary abutment against the femur which base is supported by an initial guide pin in place within the femur. A first guide member is positionably carried by the base and is indexed through 90 degrees for the taking of X-ray photographs within perpendicular planes. An optimum location for a second guide pin is plotted on the resulting X-ray photographs. The surgeon, in inserting the second guide pin, utilizes the first guide member, and a second guide member if necessary, to provide a reference point outwardly spaced from the femur to aid him in seating the guide pin through a window in the femur wall into position within the femur neck and head. A method of inserting a second guide pin is also disclosed.

10 Claims, 7 Drawing Figures

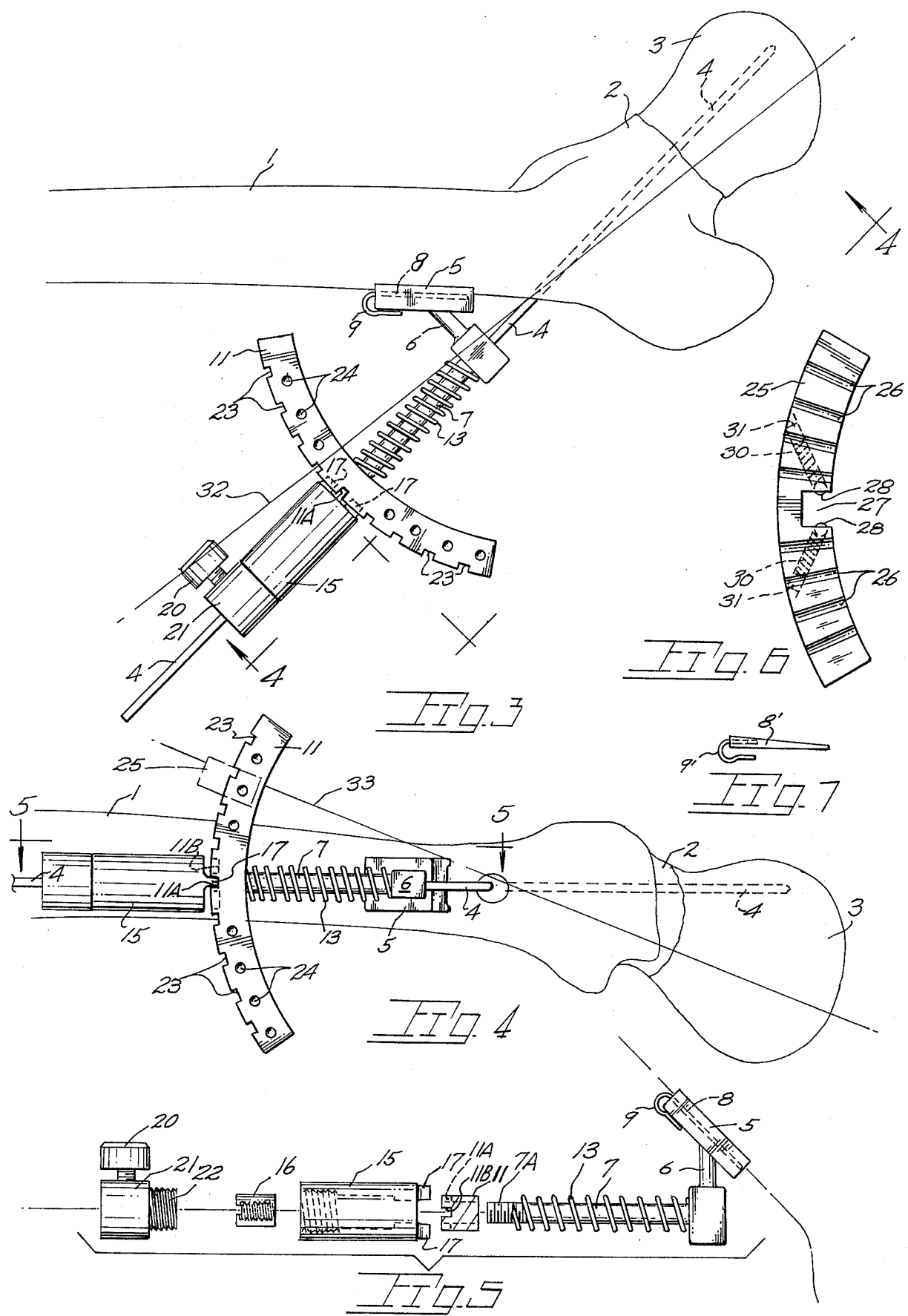

4,037,592

GUIDE PIN LOCATING TOOL AND METHOD

BACKGROUND OF THE INVENTION

The present invention concerns a tool for proper positioning of a guide pin within the head and neck portions of a femur, said pin for subsequent guidance of a hip nail prosthesis.

Conventional practice in the installation of a hip nail entails, briefly, the initial insertion of a guide pin through the upper end of the femur, the femoral neck and into the femoral head. AP and lateral X-rays are taken normally to verify guide pin location. Should repositioning of the pin be required, the corrections are plotted on the X-rays and a second guide pin insertion made. Typically both guide pin insertions are made without the aid of any guide, with the surgeon relying solely on unaided judgment. My U.S. Pat. No. 3,945,377 disclosed a hip pinning tool directed toward providing a reference or guide for both the guide pin and subsequently installed hip nail.

Complicating hip nail installation is the angulation of the femur neck and head, with respect to the femoral shaft, which angulation varies between individuals. Such variances are often accentuated by reason of neck and head displacement from injury which further complicate the task of nail installation. Presently, proper nail placement within a damaged femur is largely dependent upon the unaided skill and judgment of the surgeon. Improperly positioned hip nails, needless to say, result in further complications for both patient and surgeon.

Some tools, heretofore proposed, do not provide a reference point offset from the femur and stationary therewith. Such tools are often in supported association with the surgical table or taped to the patient and hence do not avoid discrepancies resulting from shifting of the leg member during an operation.

SUMMARY OF THE PRESENT INVENTION

The present surgical tool is adapted for temporary, positive attachment to the upper end of the femur and includes guide members providing both a horizontally and vertically corrected reference to aid the surgeon in the insertion of a second guide pin. Guide pins are of a reduced diameter and do not jeopardize femur integrity. Drilling of the femur and nail insertion are dependent on proper guide pin location.

A base of the present tool is located on an initially inserted guide pin and positioned in place against the outer wall of the femoral shank. The base includes a tubular portion to receive the initially driven guide pin. A rotatably mounted guide member on the base is positionable relative to the pin axis. Retention means are provided for temporarily securing the guide member against movement. Accordingly, the guide member may be indexed into position between the taking of AP and lateral X-ray photographs to provide a reference on the photographs for the plotting of a path for a subsequently inserted second guide pin. Upon plotting of the correction or corrections, the second guide pin is inserted into the femur. If necessary, a second or cooperating guide member may be affixed crosswise to the first guide member to provide a reference point for the surgeon resulting from corrections made within multiple planes. The joined guide members are provided with arcuately spaced indices enabling the surgeon to translated corrections plotted on X-rays to the tool to provide a visual reference during second guide pin installation.

Proper installation of the second guide pin is achieved with the patient being subjected to a minimum number of X-ray photographs, with a second set of AP and lateral photographs being optional for verification purposes of hip nail location.

Objectives of the present invention include: the provision of a surgical tool operatively supported in place by a single surgical guide pin in place within the femur neck and head with tool effectiveness unaffected by inadvertent shifting of the patient; a tool of uncomplicated design not subject to malfunction nor readily susceptible to misuse by the user; a tool having a positionable guide member which is indexed into position between the taking of AP and lateral X-rays and permits the plotting on X-ray photographs corrections for a second guide pin; a tool having a base receiving an adapter to compensate for varying femur angulation; a tool including first and second guide members the first of which appears on the X-ray photographs to facilitate the calculation of horizontal and vertical pin course corrections with both guide members ultimately serving to provide a reference (offset from the femur) for insertion of a second guide pin; a tool wherein a second guide member is provided with indices therealong corresponding to those on the photographed guide member which facilitate positioning of the second guide pin during its drilled passage into the femur; a surgical tool of relatively low manufcturing cost enabling widespread use within a wide range of medical facilities; and a method used in conjunction with the present tool for the insertion of a second guide pin along a corrected course into an optimum position within the femur.

BRIEF DESCRIPTION OF THE DRAWINGS

In the accompanying drawings:

FIG. 3 is a plan view of the tool with a first guide member positioned for the taking of an AP X-ray;

FIG. 4 is an elevational view taken approximately along line 4—4 of FIG. 3 but with the guide member indexed through 90° for the taking of a lateral X-ray;

FIG. 5 is an exploded view of the tool taken along line 5—5 of FIG. 4 with the guide pin removed;

FIG. 6 is a plan view of a second guide member detached from remaining tool structure; and FIG. 7 is a plan view of a base attachment.

DETAILED DESCRIPTION OF THE PREFERRED EMBODIMENT

Figure 1:
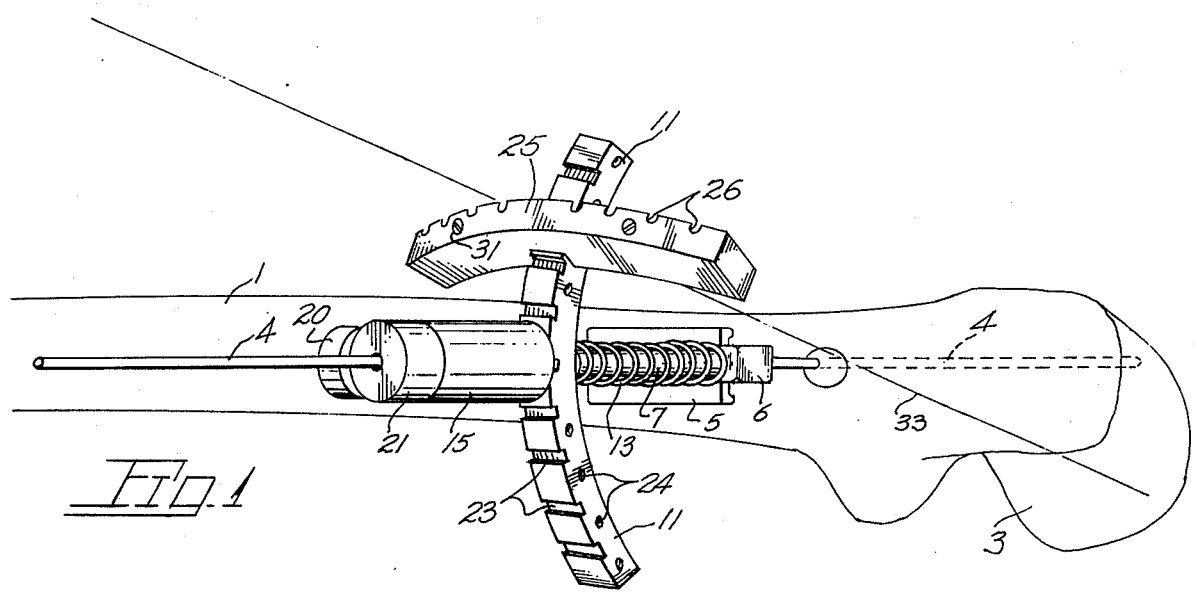
FIG. 1 is a side elevational view of a femoral shank with the present tool in place preparatory to the insertion of a second guide pin not shown.

With continuing reference to the accompanying drawings wherein applied reference numerals indicate parts similarly identified in the following specification, the reference numeral 1 indicates a femoral shank terminating at its cephalad end in a neck portion 2 and a head 3. The included angle between the axis of femoral shank 1 and that of neck 2 will normally range between 135° and 150°. A fracture of the femur neck may result in accentuated abnormal relationships of the neck and head to one another and to the femoral shank.

With attention to FIG. 3, a guide pin is indicated at 4 in drilled insertion within the femur neck and head. Said pin conventionally serves to guide an open center drill forming an opening to receive the hip nail. Accordingly, the location of guide pin 4 is critical to proper placement of the hip nail which generally includes a side plate portion for securement to the femur exterior. Upon positioning of initial guide pin 4 in place, the present tool is slid therealong to locate a tool base 5 in contact against the outer surface of the femoral shank. Base 5 includes an arm 6 enlarged at its outer end to support a tubular arm extension 7 threaded at its outer end at 7A (FIG. 5). Base 5 includes an attachment at 8 which is mounted by a clip 9 providing means for compensating for variable included angles between guide pin 4 and the femoral wall. As shown in FIG. 7 some attachments at 8' are of wedge configuration.

A first guide member 11 is supported by tubular member 7 and is adapted for rotational positioning in an indexed manner about the major axis of guide pin 4. Guide member 11 is horizontally disposed, as viewed in FIG. 3, prior to the taking of an AP X-ray photograph and subsequently is repositioned to an upright position, as viewed in FIG. 4, prior to the taking of a lateral X-ray photograph as later elaborated upon.

Retention means are also supported by tubular member 7 and serve to retain guide member 11 against undesired movement. Said retention means includes a helical spring 13 and a guide member lock 15 of cylindrical shape and confined on tubular member 7 by a nut element 16 (FIG. 5). Guide lock 15 includes a pair of projections 17 which alternately engage pairs of ninety degree offset recesses at 11A and 11B formed within guide member 11. During tool use guide member 11 is manually advanced forwardly against spring 13 to disengage projections 17, a pair of recesses (11A or 11B) in said guide member thereby enabling repositioning of the guide member and automatic locking in place upon release of same.

For purposes of securing guide lock 15 against the outward biasing action of spring 13, a thumb screw member 20 is adjustably engageable at its inner end with guide pin 4, said thumb screw being threaded within a cap 21 which is threaded at 22 for securement to tubular guide lock 15.

With attention to first guide member 11, the same is of arcuate shape provided with spaced apart indices 23 which constitute reference marks usable in a plotting on the X-ray photograph of a "corrected" guide pin location. Said indices are embodied within recesses formed within guide member 11 which recesses are clearly discernible on the X-ray photographs to facilitate plotting and subsequent scribing of a "corrected" pin location. Sockets at 24 are formed within the opposite side surfaces of guide member 11 for purposes of attaching a second guide member 25.

Figure 2:
FIG. 2 is a plan view of FIG. 1.

Said first guide member 11 is adapted to detachably receive and support a second guide member at 25 with the recesses or socket at 24 serving to receive spring biased ball elements associated with said second guide member. As best shown in FIGS. 1, 2 and 6, second guide member 25 is also of arcuate configuration having indices at 26 arcuately spaced in the same manner as indices 23 on first guide member 11. A central inset area at 27 permits the second guide member to be slidably engaged with the first guide member when both guide members are required. Ball elements at 28 project into recess 27 for seated engagement with recesses 24 or opposite surfaces of first guide member 11. The indices 26 are of channel-like configuration and of a dimension to permit passage therealong of a second guide pin during its insertion. Ball elements 28 of the second guide member are resiliently mounted by means of spring elements 30 and threaded inserts 31.

The present method of locating a second or "corrected" guide pin consists of the following steps. A "window" or opening is formed within the femoral wall whereupon the first guide pin 4 is inserted in the conventional manner to its position shown in FIGS. 1 through 4. With the tool in the configuration shown in FIG. 3, an AP X-ray photograph is taken. Upon indexing of first guide member 11 through 90° to the FIG. 4 position, a lateral X-ray photograph is taken. On the above X-ray photographs, a corrected pin course is plotted as represented by lines 32 and 33 in FIGS. 1 through 4 with line 32 being termed a horizontal correction and line 33 being termed a vertical correction. With the courses so scribed on the X-ray photographs, the necessary correction or corrections may be readily transferred to the tool which may be in the fully assembled configuration shown in FIGS. 1 and 2 if both vertical and horizontal plane corrections are necessary. Preparatory to inserting the second or corrected guide pin, second guide member 25, if required, is affixed to the first guide member to provide the proper anterior to posterior angulation as best shown in FIG. 4. To accomplish this, the second guide member is attached to now upright first guide member 11 in a manner locating a channel-like indices 26, on second guide member 25, coplanar with the desired first guide member indices 23 as shown in FIG. 4. The horizontal component of the correction is accomplished by locating of the second guide pin within a channel-like indices 26 of the second guide member corresponding to the bisected indices of the first guide member as scribed on the AP X-ray photograph. Accordingly, the positioned second guide pin is now located so as to result in desired penetration, via the femur window, into the femur neck and head enabling subsequent optimum drilling and nail insertion.

In certain instances only a horizontal or vertical correction will be required for proper insertion of the second guide pin, while in still other instances a second guide pin will be in offset parallel relationship to the initial guide pin. In the latter case, a corrected pin course will be scribed on the appropriate X-ray photograph with the scribed course line intersecting the photographed image of first guide member 11. The surgeon, in inserting the second guide pin, will maintain said pin parallel to and offset from the previously inserted guide pin a distance equal to the distance between the scribed course line and the photographic image of already inserted guide pin 4. Accordingly, the present tool supplements the skill of the surgeon and greatly reduces the chance of error. A second set of AP and lateral X-ray photographs may be taken to verify the position of the second guide pin, whereafter drilling and hip nail insertion tasks are performed.

While I have shown but one embodiment of the invention, it will be apparent to those skilled in the art that the invention may be embodied still otherwise without departing from the spirit and scope of the invention.

Having thus described the invention, what is desired to be secured under a Letters Patent is:

I claim:

1. A tool for use in the positioning of a surgical guide pin within the neck and head portions of a femur preparatory to hip nail installatin, said tool comprising,
   a base adapted for surfacial abutment against the femur exterior offset from the guide pin axis and supported by a first surgical guide pin projecting outwardly from the femur, said base including an outwardly extending arm and arm extension, a guide member rotatably mounted on said base and positionable about the axis of said first surgical guide pin preparatory to the taking of AP and lateral X-ray photographs of the femur with inserted surgical guide pin and attached tool, retention means holding said guide member against undesired rotational movement in perpendicularly related position during the taking of the X-ray photographs, and said guide member having indices thereon discernible on the AP and lateral X-ray photographs to enable the plotting of a corrected course for a second guide pin, said indices also facilitating the positioning and axial guidance of a second surgical guide pin for entry of same into the femur along said corrected course.

2. The tool claimed in claim 1 wherein said retention means includes a resilient member and a guide member lock the latter including a first guide pin engaging member for securing the guide member lock thereto.

3. The tool claimed in claim 2 wherein said guide member and said guide member lock include interengaging means engageable upon rotation of the guide member through 90°.

4. The tool claimed in claim 1 wherein said base includes means for varying the angular relationship of the base arm to the major axis of the femur.

5. The tool claimed in claim 1 additionally including a second guide member adapted for selective supported attachment in a crosswise manner to the first mentioned guide member to provide a course for the entry of the second guide pin when pin course corrections must be made in two planes.

6. The tool claimed in claim 5 wherein said first and second guide members are of elongate arcuate shape and provided with indices therealong in the form of transverse grooves.

7. The tool claimed in claim 6 wherein said indices are spaced along said second guide member in a manner corresponding to the spacing of indices along the first mentioned guide member whereby corrections plotted on the X-ray photographs of said first guide member may be applied to the second guide member when pin course corrections must be made in two planes.

8. The tool claimed in claim 7 wherein said second guide member and the first mentioned guide member mutually embody interengaging means enabling crosswise attachment of said second guide member at a point along said first guide member.

9. The method of positioning a guide pin within the neck and head portions of a femur preparatory to the installation of a hip nail, said method consisting of the steps of, inserting a guide pin into the femur neck and head positions, mounting a guide member on said pin, X-ray photographing the femur, inserted guide pin with guide member thereon in one photographic plane, repositioning the guide member about the pin axis, X-ray photographing the femur, inserted guide pin with repositioned guide member thereon along a second photographic plane normal to the first X-ray photograph, plotting a corrected guide pin course on the X-ray photograph to determine the course for a second guide pin, and inserting a second guide pin into the femur offset from the first guide pin with the axis of the second guide pin located so as to intersect the guide member at a point corresponding to the intersection of the plotted guide pin course and guide member on the photograph.

10. The method claimed in claim 9 including the additional step, subsequent to plotting of the correction, of applying a second guide member transversely on said first guide member to provide a corrected guide pin course with corrections made within two planes.

* * * * *